(12) United States Patent
Gawin et al.

(10) Patent No.: US 11,291,983 B2
(45) Date of Patent: Apr. 5, 2022

(54) ORGANORUTHENIUM CARBIDE COMPLEXES AS PRECATALYSTS FOR OLEFIN METATHESIS

(71) Applicants: APEIRON SYNTHESIS S. A., Wroclaw (PL); PROMERUS, LLC, Brecksville, OH (US)

(72) Inventors: Rafał Gawin, Wroclaw (PL); Oleksandr Burtovyy, Brecksville, OH (US); Larry F Rhodes, Brecksville, OH (US)

(73) Assignees: APEIRON SYNTHESIS S.A., Wroclaw (PL); PROMERUS, LLC

( * ) Notice: Subject to any disclaimer, the term of this patent is extended or adjusted under 35 U.S.C. 154(b) by 0 days.

(21) Appl. No.: 17/024,778

(22) Filed: Sep. 18, 2020

(65) Prior Publication Data

US 2021/0077988 A1    Mar. 18, 2021

Related U.S. Application Data

(60) Provisional application No. 62/901,860, filed on Sep. 18, 2019.

(51) Int. Cl.

| | |
|---|---|
| *B01J 31/22* | (2006.01) |
| *B01J 31/24* | (2006.01) |
| *C07C 6/04* | (2006.01) |
| *C07F 15/00* | (2006.01) |
| *C07D 211/04* | (2006.01) |
| *C07D 235/00* | (2006.01) |
| *C07D 207/02* | (2006.01) |
| *C07C 6/02* | (2006.01) |
| *C07C 6/06* | (2006.01) |

(52) U.S. Cl.
CPC ....... *B01J 31/2273* (2013.01); *B01J 31/2278* (2013.01); *B01J 31/24* (2013.01); *B01J 31/2404* (2013.01); *C07C 6/04* (2013.01); *C07D 207/02* (2013.01); *C07D 211/04* (2013.01); *C07D 235/00* (2013.01); *C07F 15/0046* (2013.01); *B01J 2231/543* (2013.01); *B01J 2531/821* (2013.01); *C07C 6/02* (2013.01); *C07C 6/06* (2013.01); *C07C 2531/22* (2013.01)

(58) Field of Classification Search
CPC .... B01J 31/2273; B01J 31/2278; B01J 31/24; B01J 31/2404; B01J 2231/543; B01J 2531/821; B01J 2540/54; C07C 6/04; C07C 6/02; C07C 6/06; C07C 2531/22; C07C 2531/24; C07D 207/02; C07D 211/04; C07D 235/00
See application file for complete search history.

(56) References Cited

U.S. PATENT DOCUMENTS

| | | | | |
|---|---|---|---|---|
| 2006/0128912 | A1* | 6/2006 | Piers | .................... B01J 31/2265 526/171 |
| 2014/0099573 | A1* | 4/2014 | Weitekamp | ............... G03F 7/20 430/18 |

FOREIGN PATENT DOCUMENTS

WO    WO 2020/003035 A1    1/2020

OTHER PUBLICATIONS

Keitz and Grubbs, "Probing the Origin of Degenerate Metathesis Selectivity via Characterization and Dynamics of Ruthenacyclobutanes Containing Variable NHCs", J. Am. Chem. Soc. 2011, 133, 16277-16284. (Year: 2011).*

(Continued)

*Primary Examiner* — Ali Z Fadhel
(74) *Attorney, Agent, or Firm* — Balaram Gupta

(57) ABSTRACT

Embodiments in accordance with the present invention encompass an organoruthenium compound of the formula (I) or formula (II):

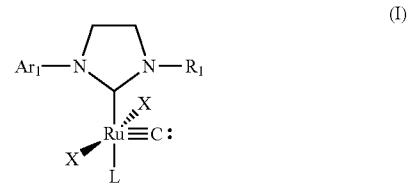

(I)

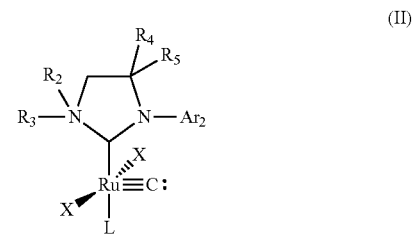

(II)

Wherein X, L, $R_1$, $R_2$, $R_3$, $R_4$, $R_5$, $Ar_1$ and $Ar_2$ are as defined herein. Also disclosed herein are the use of organoruthenium compound of the formula (I) or formula (II) as (pre)catalysts for the olefin metathesis reactions, as well as to the process for carrying out the olefin metathesis reaction.

11 Claims, No Drawings

(56) References Cited

OTHER PUBLICATIONS

Khalimon et al., "Photogeneration of a Phosphonium Alkylidene Olefin Metathesis Catalyst", Organometallics 2012, 31, 5634-5637. (Year: 2012).*

Andrey Y. Khalimon, et al., "Photogeneration of a Phosphonium Alkylidene Olefin Metathesis Catalyst," Organometallics, 2012, vol. 31, pp. 5634-5637.

Robert G. Carlson, et al., "The Metathesis-Facilitated Synthesis of Terminal Ruthenium Carbide Complexes: A Unique Carbon Atom Transfer Reaction," J. Am. Chem. Soc., 2002, vol. 124, pp. 1580-1581.

John R. Tumbleston, et al., "Continuous Liquid Interface Production of 3D Objects," Science, 2015, vol. 347, pp. 1349-1352.

* cited by examiner

ORGANORUTHENIUM CARBIDE COMPLEXES AS PRECATALYSTS FOR OLEFIN METATHESIS

CROSS REFERENCE TO RELATED APPLICATIONS

This application claims the benefit of U.S. Provisional Application No. 62/901,860, filed Sep. 18, 2019, which is incorporated herein by reference in its entirety.

BACKGROUND OF THE INVENTION

Field of the Invention

The present invention relates to a series of organoruthenium carbide complexes, their use as (pre)catalysts in the metathesis reaction as well as the process for carrying out the metathesis reaction. More specifically, the present invention relates to a series of organoruthenium carbides which when activated under suitable conditions exhibit improved catalytic activity for a wide range of metathesis reactions. This invention also relates to methods of making these compounds. Accordingly, the compounds of this invention find utility as precatalysts for carrying out a variety of olefin metathesis reactions, including ring-opening metathetic polymerization (ROMP), among others.

Description of the Art

The metathesis of olefins is an important tool in the organic synthesis (Handbook of Metathesis, Vol. I-III, Grubbs, R. H., ed.; Wiley-VCH, 2003).

Many ruthenium complexes actively catalyzing the metathesis of olefins are well known in the art (see, for example, Vougioukalakis, G. C.; Grubbs, R. H. Chem. Rev. 2010, 110, 1746). The third generation complexes (such as Gru-III, Ind-III) were shown to be highly useful (pre) catalysts of the ring-opening metathetic polymerization (ROMP) reaction.

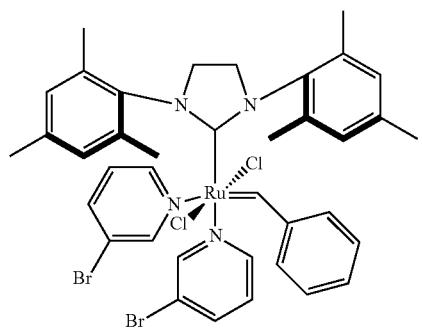

Gru III

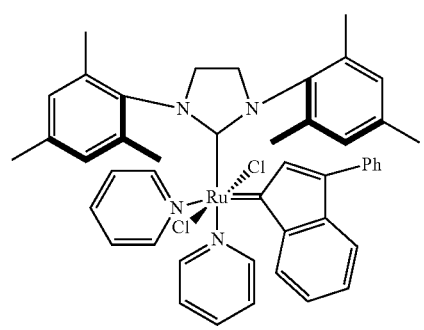

Ind III

The third-generation catalysts initiate the metathesis reactions very promptly, whereas, in some metathesis applications, such as mold ROMP polymerization, it is advantageous to use a (pre)catalyst that does not initiate the reaction immediately after adding it to the substrate but only after an appropriate initiation by chemical agents, temperature or light. The complexes characterized by delayed initiation are often termed "dormant catalysts" (Monsaert, S.; Vila, A. L.; Drozdzak, R.; Van Der Voort, P.; Verpoort, F., Chem. Soc. Rev., 2009, 38, 3360; R. Drozdzak, N. Nishioka, G. Recher, F. Verpoort, Macromol. Symp. 2010, 293, 1-4). Exemplary "dormant catalysts" are the complexes A-F, as well as the recently obtained P-1 and P-2 (Pietraszuk, C.; Rogalski, S.; Powala, B.; Mitkiewski, M.; Kubicki, M.; Spolnik, G.; Danikiewicz, W.; Wozniak, K.; Pazio, A.; Szadkowska, A.; Kozlowska, A.; Grela, K., Chem. Eur. J, 2012, 18, 6465-6469).

The co-pending PCT patent application, PCT/IB2019/054879, filed Jun. 11, 2019 discloses various other organoruthenium precatalysts useful for ROMP.

The mold ROMP polymerization allows obtaining finished articles. Dicyclopentadiene is one of the monomers frequently used for the mold polymerization. Polydicyclopentadiene, being obtained by polymerization of dicyclopentadiene, features, inter alia, a low moisture absorption as well as resistance to stress and high temperature. This is why parts of vehicles and specialized containers for the chemical industry are more and more frequently manufactured by the (mold) ROMP polymerization of dicyclopentadiene.

U.S. Pat. No. 9,328,132 B2 addresses some of these deficiencies faced by the art in providing more robust "dormant catalysts" for olefin metathesis reactions, pertinent portions of which are incorporated herein by reference. However, there is still a need for improved "dormant catalysts" which can be activated under desirable ROMP polymerization conditions and based on the intended end applications.

Accordingly, it is an object of this invention to provide a series of improved "dormant catalysts."

It is also an object of this invention to provide processes for the preparation of such organoruthenium dormant catalysts as disclosed herein.

Other objects and further scope of the applicability of the present invention will become apparent from the detailed description that follows.

From the viewpoint of practical industrial applications, it is of extreme importance that the (pre)catalysts are stable in the presence of oxygen as well as moisture during their use in the metathesis reaction. Development of stable and active (pre)catalysts for metathesis of olefins as reported in the literature allowed to broaden significantly the scope of possible uses of this transformation. Nevertheless, these complexes are still prepared and used in metathesis reactions in atmosphere of inert gas, in dry solvents, since their stability against oxygen and moisture is limited.

Surprisingly, it has now been found that the ruthenium complexes depicted by the formula (I) are stable in the presence of air and moisture.

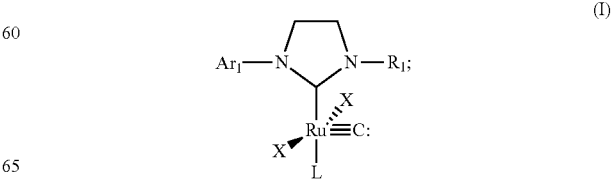

(I)

wherein:

X is chlorine, bromine or iodine;

L is PR$_3$, where R is independently selected from the group consisting of isopropyl, sec-butyl, tert-butyl, cyclohexyl, bicyclo(C$_5$-C$_{10}$)alkyl, phenyl, benzyl, isopropoxy, sec-butoxy, tert-butoxy, cyclohexyloxy, phenoxy and benzyloxy;

R$_1$ is selected from the group consisting of methyl, ethyl, isopropyl, sec-butyl, tert-butyl, substituted or unsubstituted cyclohexyl, substituted or unsubstituted phenyl, substituted or unsubstituted biphenyl and substituted or unsubstituted naphthyl;

Ar$_1$ is selected from the group consisting of substituted or unsubstituted phenyl, substituted or unsubstituted biphenyl and substituted or unsubstituted naphthyl;

wherein said substituents are selected from the group consisting of methyl, ethyl, iso-propyl, tert-butyl and phenyl; and with the proviso that when X is chlorine R$_1$ is not 2,4,6-trimethylphenyl.

It should be noted that a neutral "carbene" type heterocylic ligand is linked to ruthenium as depicted above in the compound of formula (I), which is a particular type of N-heterocyclic carbene (NHC) ligand. Various other NHC ligands that can also be used in forming various other compounds of formula (I) are exemplified below.

It has been observed now that compounds of the formula (I) are very stable and can be stored, handled and used in metathesis reactions without any protective atmosphere of inert gas. Even more surprisingly, when X is iodine, the compounds of formula (I) are even more stable and "dormant" under ambient conditions. Even more advantageously the compounds of formula (I) are readily soluble in a variety of ring open metathesis polymerizable (ROMP) cycloalkene monomers, and can be kept in solution for a number of days even up to ten days or longer at temperatures up to 35° C., thus find utility in a number of applications including for example photopatternable compositions, as 3D ink materials and in nanoimprint lithography, just to mention a few.

Following their suitable activation, the compounds of the general formula (I) actively catalyze the metathesis reactions carried out in the presence of air. Moreover, the compounds of the general formula (I) actively catalyze the metathesis reactions only after being activated by chemical agents, and they are very hardly susceptible to thermal activation. These properties enable excellent control of the time of initiating the reaction; such a property is very useful especially for the ROMP-type reactions. It was unexpectedly observed that the compounds of the general formula (I) allowed obtaining polycycloolefinic polymers via the ROMP-type reaction carried out in the air, the amount of the (pre)catalyst used being significantly lower than that in the case of using classical complexes. Even an amount of 100 ppm (parts per million, by weight) of the complex according to the invention, the compounds of the general formula (I) or the compounds of the general formula (II), effectively catalyzes polymerization of a variety of cycloalkenes. Thus, this amount of the (pre)catalyst is less than half of that in the case of the catalysts reported in the literature, see for example, M. Perring, N. B. Bowden Langmuir, 2008, 24, 10480-10487.

The compound of general formula (I) according to the invention, wherein X is chlorine, Ar$_1$ and R$_1$ are both 2,4,6-trimethylphenyl and L is tricyclohexylphosphine, which is of the formula (IA) is known in the literature.

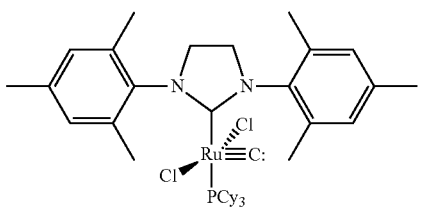

1,3-bis(2,4,6-trimethylphenyl)-imidazolidin-2-ylidene-tricyclohexylphosphine-ruthenium carbide dichloride (IA)

Accordingly, the compound of formula (IA) is expressly disclaimed from the compounds of general formula (I). It should further be noted that Piers, et al., Organometallics 2012, 31, 5634-5637, have shown that the compound of formula (IA) can be used to generate a phosphonium alkylidene olefin metathesis catalyst photolytically using photoacid generator. The catalyst so generated is active for ring open metathesis polymerization of certain cycloalkenes. However, such reactions are carried out in a solvent, and using a large amount of the catalyst, from one to five mole percent of the catalyst. Therefore, such conditions are not suitable for many applications, such as for example, as 3D ink materials for mass polymerization conditions.

Surprisingly, it has now been found that the compounds of formula (I) where X is iodine imparts unusually very high "dormant" effect on the catalyst. Thus, the iodide compounds of formula (I) can be stable for a long length of time even up to ten days or longer and can be made active only when subjected to suitable photoacid generators (PAG) and/or thermal acid generators (TAG). Even more interestingly, such compounds can only be activated using PAGs or TAGs or such similar compounds which generate a chloride ion. Thus offering unique advantages in using compounds of formula (I) and tailoring their use in many different applications. In addition, the possibility of affecting the properties of a (pre)catalyst by changing its ligands and, in consequence, the possibility of optimal tuning its activity for a specific reaction, is extremely valuable. Accordingly it has now been observed that tuning of the ligands of the compounds of formula (I) can result in different catalytic activity as well as dormancy of the catalytic activity. For example, various substitutions of the N-heterocyclic carbene ligand (NHC) results in vastly different catalytic activity of the resulting compound of formula (I). Thus, different compounds of formula (I) in accordance with this invention can be tailored to meet the needs of the intended application.

Accordingly, there is provided the compounds of the general formula (I) in accordance with the present invention as described hereinabove as precatalysts for the olefin metathesis reactions.

In some embodiments, the compound of the formula (I) according to this invention is having:

X is chlorine or iodine;

R$_1$ and Ar$_1$ are both substituted phenyl; and

L is PR$_3$, where each R is independently selected from the group consisting of isopropyl, sec-butyl, tert-butyl, cyclohexyl and phenyl.

In some other embodiments, the compound of the formula (I) according to this invention is having:

X is chlorine or iodine;

L is PR$_3$, where R is independently selected from the group consisting of isopropyl, sec-butyl, tert-butyl, cyclohexyl, phenyl, isopropoxy, sec-butoxy, tert-butoxy, cyclohexyloxy and phenoxy;

$Ar_1$ and $R_1$ are the same or different and each independently selected from the group consisting of phenyl, 2,4,6-trimethylphenyl, 2,6-dimethylphenyl; 4-methylphenyl, 2,4,6-triethylphenyl, 2,6-diethylphenyl, 2,4,6-triisopropylphenyl and 2,6-diisopropylphenyl.

In yet some other embodiments, the compound of the formula (I) according to this invention is having:

X is chlorine;

$R_1$ and $Ar_1$ are independently selected from the group consisting of phenyl, 2-methylphenyl, 2,4-dimethylphenyl, 2,6-dimethylphenyl, 2,4,6-trimethylphenyl, 2-ethylphenyl, 2,4-diethylphenyl, 2,6-diethylphenyl, 2,4,6-triethylphenyl, 2-isopropylphenyl and 2,6-diisopropylphenyl; and L is tri(isopropyl)phosphine or tricyclohexylphosphine.

In yet some other embodiments, the compound of the formula (I) according to this invention is having:

X is chlorine;

$R_1$ and $Ar_1$ are independently selected from the group consisting of phenyl, 2,4-dimethylphenyl, 2,6-dimethylphenyl, 2,4,6-trimethylphenyl, 2,4-diethylphenyl, 2,6-diethylphenyl, 2,4,6-triethylphenyl, 2-isopropylphenyl and 2,6-diisopropylphenyl; and L is tricyclohexylphosphine.

In yet some other embodiments, the compound of the formula (I) according to this invention is having:

X is iodine;

$R_1$ and $Ar_1$ are independently selected from the group consisting of 2,6-dimethylphenyl, 2,4,6-trimethylphenyl, 2,6-diethylphenyl, 2,4,6-triethylphenyl and 2,6-diisopropylphenyl; and L is tricyclohexylphosphine.

In some other embodiments, the compound of the formula (I) according to this invention is having:

X is iodine;

L is $PR_3$, where R is independently selected from the group consisting of isopropyl, cyclohexyl and phenyl;

$Ar_1$ and $R_1$ are the same or different and each independently selected from the group consisting of phenyl, 2,4,6-trimethylphenyl, 2,4,6-triethylphenyl, 2,6-diethylphenyl, 2,4,6-triisopropylphenyl and 2,6-diisopropylphenyl.

Representative non-limiting examples of the compound of the formula (I) may be enumerated as follows:

1,3-bis(2,6-diisopropylphenyl)-imidazolidin-2-ylidene-tricyclohexylphosphine-ruthenium carbide dichloride (IB);

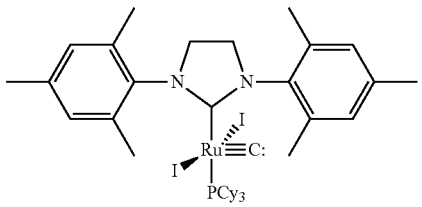

1,3-bis(2,4,6-trimethylphenyl)-imidazolidin-2-ylidene-tricyclohexylphosphine-ruthenium carbide diiodide (IC);

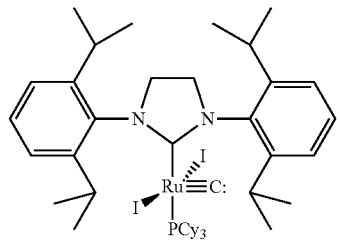

1,3-bis(2,6-diisopropylphenyl)-imidazolidin-2-ylidene-tricyclohexylphosphine-ruthenium carbide diiodide (ID)

The compounds of the general formula (I) can be prepared by any of the known procedures in the art. For example, Carlson et al., disclose a procedure for the preparation of the compound of formula (IA), which involves reacting a suitable organoruthenium precursor compound to form the compound of formula (IA), as more generically shown in Scheme I.

Scheme I shows the method in accordance with the present invention for the preparation of the compounds of formula (I).

Scheme I

ROUTE A

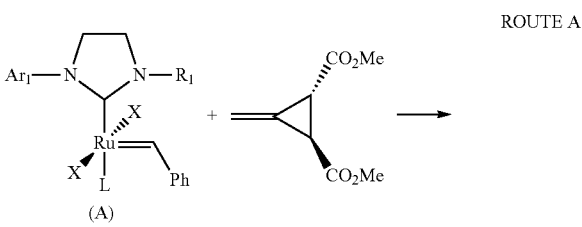

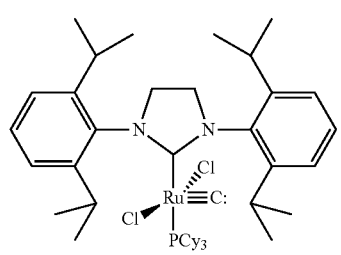

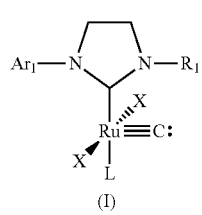

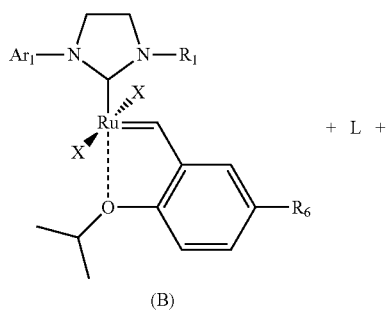

ROUTE B

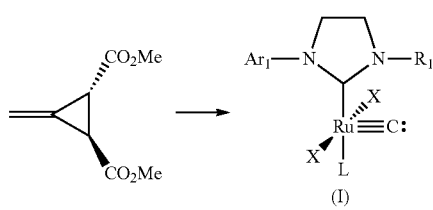

As shown in Scheme I, the compounds of formula (I) can be prepared by at least two methods as illustrated, Route A or Route B. In Route A, a suitable organoruthenium precursor compound of formula (A) is reacted with trans-2,3-dicarbomethoxymethylenecyclopropane at suitable reaction conditions. In the formula (A) X, L, $Ar_1$ and $R_1$ are as defined hereinabove. The reaction can be carried out at ambient or super-ambient conditions. Generally, such reactions are carried out in a suitable organic solvent at a temperature from about 0° C. to about 100° C. or higher. In some embodiments such reactions are carried out at a temperature from about 20° C. to about 50° C. Any of the solvents that would dissolve compound of formula (A) and trans-2,3-dicarbomethoxymethylenecyclopropane can be employed in this reaction. Suitable solvents include toluene, tetrahydrofuran, dichloromethane, dichloroethane, and mixtures in any combination thereof.

In Route B, Scheme I, a compound of formula (B), where X, $Ar_1$ and $R_1$ are as defined hereinabove and $R_6$ is hydrogen or $NO_2$ is reacted with a suitable ligand, L, as defined above in the presence of trans-2,3-dicarbomethoxymethylenecyclopropane at suitable reaction conditions. The reaction can again be carried out at ambient or super-ambient conditions. Generally, such reactions are carried out in a suitable organic solvent at a temperature from about 0° C. to about 100° C. or higher. In some embodiments such reactions are carried out at a temperature from about 20° C. to about 50° C. Any of the solvents that would dissolve compound of formula (B), ligand L and trans-2,3-dicarbomethoxymethylenecyclopropane can be employed in this reaction. Suitable solvents include toluene, tetrahydrofuran, dichloromethane, dichloroethane, and mixtures in any combination thereof.

In another aspect of this invention there is also provided a compound of formula (II):

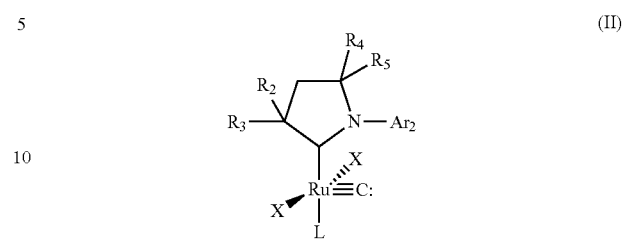

wherein:

X is chlorine, bromine or iodine;

L is $PR_3$, where R is independently selected from the group consisting of isopropyl, sec-butyl, tert-butyl, cyclohexyl, bicyclo($C_5$-$C_{10}$)alkyl, phenyl, benzyl, isopropoxy, sec-butoxy, tert-butoxy, cyclohexyloxy, phenoxy and benzyloxy;

$R_2$ and $R_3$ are the same or different and each independently selected from the group consisting of hydrogen, methyl, ethyl, linear or branched ($C_1$-$C_6$)alkyl, ($C_6$-$C_{10}$)aryl, methoxy, ethoxy, linear or branched ($C_1$-$C_6$)alkoxy, ($C_6$-$C_{10}$)aryloxy, —NHCO($C_1$-$C_6$)alkyl, —NHCO-perfluoro($C_1$-$C_6$)alkyl, —$SO_2$N(($C_1$-$C_6$)alkyl)$_2$ and —$NO_2$; or $R_2$ and $R_3$ taken together with the carbon atom to which they are attached to form a ($C_3$-$C_7$)cycloalkyl ring;

$R_4$ and $R_5$ are the same or different and each independently selected from the group consisting of hydrogen, methyl, ethyl and linear or branched ($C_1$-$C_6$)alkyl;

$Ar_2$ is selected from the group consisting of substituted or unsubstituted phenyl, substituted or unsubstituted biphenyl and substituted or unsubstituted naphthyl;

wherein said substituents are selected from the group consisting of methyl, ethyl, iso-propyl, tert-butyl and phenyl.

The compounds of formula (II) are also found to be very stable in the presence of air and moisture and can be stored at ambient conditions for a longer period of time as a solution in a number of cycloalkenes which undergo ring open metathesis polymerization, and yet can be activated readily by subjecting them to either photolytic or thermolytic conditions in the presence of either a photoacid generator or a thermal acid generator. Therefore, compounds of formula (II) also serve as excellent (pre)catalysts for ring-opening metathetic polymerization (ROMP).

Accordingly, there is provided the compounds of the general formula (II) in accordance with the present invention as described hereinabove as precatalysts for the olefin metathesis reactions.

In some embodiments, the compound of the formula (II) according to this invention is having:

X is chlorine or iodine;

each $R_2$, $R_3$, $R_4$ and $R_5$ is independently selected from the group consisting of methyl, ethyl, n-propyl, iso-propyl, n-butyl, iso-butyl, tert-butyl and phenyl;

$Ar_2$ is substituted phenyl; and

L is $PR_3$, where each R is independently selected from the group consisting of isopropyl, sec-butyl, tert-butyl, cyclohexyl and phenyl.

In some other embodiments, the compound of the formula (II) according to this invention is having:

X is chlorine;

$R_2$ and $R_3$ taken together with the carbon atom to which they are attached to form a cyclopentyl, cyclohexyl or cycloheptyl ring;

each $R_4$ and $R_5$ is independently selected from the group consisting of hydrogen, methyl, ethyl and iso-propyl;

$Ar_2$ is selected from the group consisting of phenyl, 2-methylphenyl, 2,4-dimethylphenyl, 2,6-dimethylphenyl, 2,4,6-trimethylphenyl, 2-ethylphenyl, 2,4-diethylphenyl, 2,6-diethylphenyl, 2,4,6-triethylphenyl, 2-isopropylphenyl and 2,6-diisopropylphenyl; and L is tri(isopropyl)phosphine or tricycohexylphosphine.

In yet some other embodiments, the compound of the formula (II) according to this invention is having:

X is chlorine;

each $R_2$, $R_3$, $R_4$ and $R_5$ independently is methyl or ethyl;

$Ar_2$ is selected from the group consisting of phenyl, 2,4-dimethylphenyl, 2,6-dimethylphenyl, 2,4,6-trimethylphenyl, 2,4-diethylphenyl, 2,6-diethylphenyl, 2,4,6-triethylphenyl, 2-isopropylphenyl and 2,6-diisopropylphenyl; and L is tricyclohexylphosphine.

In yet some other embodiments, the compound of the formula (H) according to this invention is having:

X is iodine;

each $R_2$, $R_3$, $R_4$ and $R_5$ independently is methyl or ethyl;

$Ar_2$ is selected from the group consisting of 2,6-dimethylphenyl, 2,4,6-trimethylphenyl, 2,6-diethylphenyl, 2,4,6-triethylphenyl and 2,6-diisopropylphenyl; and L is tricyclohexylphosphine.

Representative non-limiting examples of the compound of the formula (II) may be enumerated as follows:

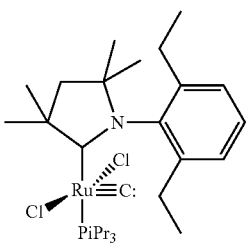

1-(2,6-diethylphenyl)-3,3,5,5-tetramethylpyrrolidin-2-ylidene-triisopropylphosphine ruthenium carbide dichloride (IIA);

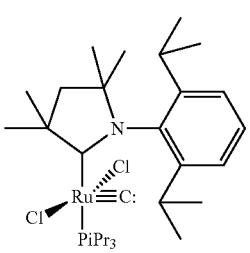

1-(2,6-diisopropylphenyl)-3,3,5,5-tetramethylpyrrolidin-2-ylidene-triisopropylphosphine ruthenium carbide dichloride (HIB);

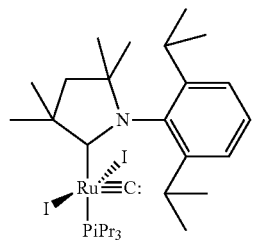

1-(2,6-diisopropylphenyl)-3,3,5,5-tetramethylpyrrolidin-2-ylidene-triisopropylphosphine ruthenium carbide diiodide (IIC);

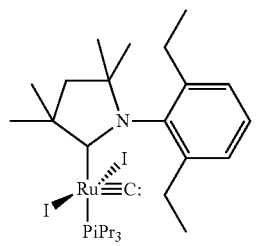

1-(2,6-diethylphenyl)-3,3,5,5-tetramethylpyrrolidin-2-ylidene-triisopropylphosphine ruthenium carbidediiodide (IID);

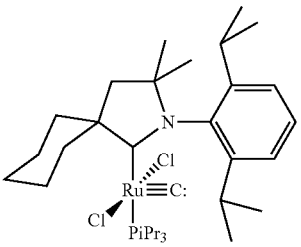

1-(2,6-diisopropylphenyl)-3,3-dimethyl-2$\lambda^2$-azaspiro[4.5]decylidene-triisopropylphosphine ruthenium carbide dichloride (IIE);

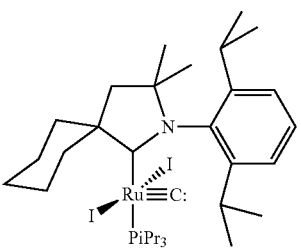

1-(2,6-diisopropylphenyl)-3,3-dimethyl-2λ²-azaspiro[4.5]
decylidene-triisopropylphosphine ruthenium carbide diiodide (IIF);

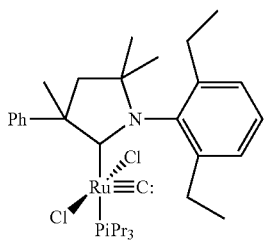

1-(2,6-diethylphenyl)-3,5,5-trimethyl-3-phenylpyrrolidin-2-ylidene-triisopropylphosphine ruthenium carbide dichloride (IIG);

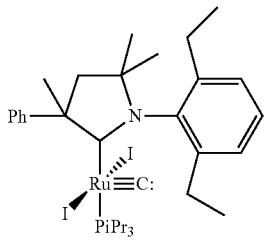

1-(2,6-diethylphenyl)-3,5,5-trimethyl-3-phenylpyrrolidin-2-ylidene-triisopropylphosphine ruthenium carbide diiodide (IIH);

The compounds of the general formula (II) can be prepared by any of the known procedures in the art, particularly, using similar procedures as used for the preparation of compounds of formula (I) described hereinabove. More specifically, the compounds of formula (II) can be prepared in accordance with Scheme II starting with corresponding compounds of formula (C) or (D) using either Route A or B.

Scheme II

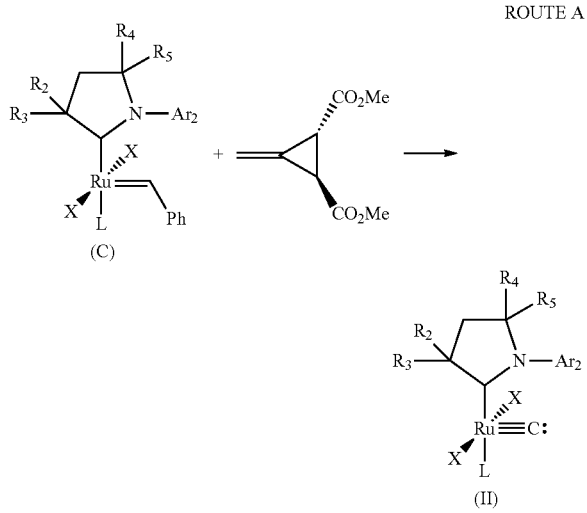

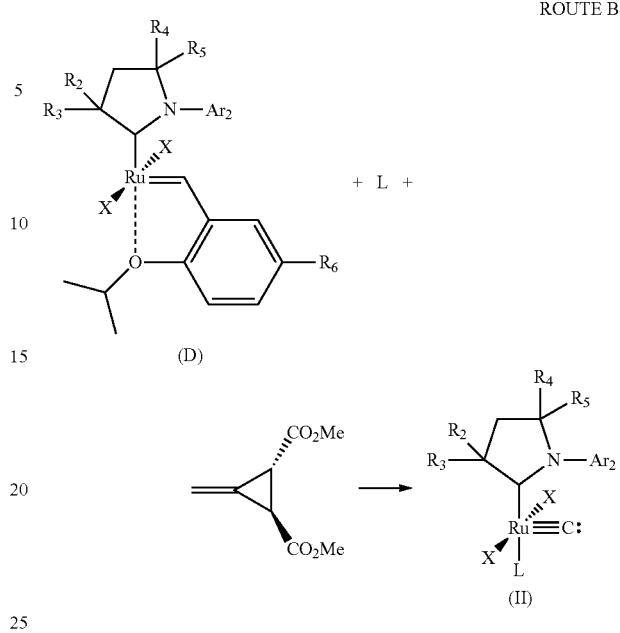

The invention is related also to use of the compounds of the general formula (I) or the compounds of the general formula (II) as defined hereinabove as (pre)catalysts in the metathesis reactions. In some embodiments, the compounds of the general formula (I) or the compounds of the general formula (II) are used as (pre)catalysts in the reactions of ring-closing metathesis, cross metathesis, homometathesis, alkene-alkyne type metathesis. In some other embodiments, the compounds of the general formula (I) or the compounds of the general formula (II) are used as (pre)catalysts in the reaction of ring-opening metathetic polymerization.

The invention concerns also a process for carrying out the metathesis reaction of olefins, wherein at least one olefin is contacted with a compound of the general formula (I) or the compounds of the general formula (II) as a (pre)catalyst.

Generally, the metathesis reaction is carried out in an organic solvent. Any of the organic solvents that would allow such polymerization reaction to be carried out can be used. Non-limiting examples of such organic solvents include dichloromethane, dichloroethane, toluene, ethyl acetate and mixtures in any combination thereof.

In some embodiments, the metathesis reaction is carried out without any solvent. In some other embodiments, the metathesis reaction is carried out in the presence of a chemical activator. In general, the chemical activator is a Bronsted or Lewis acid or a halo-derivative of alkane or silane. Non-limiting examples of such activators include hydrogen chloride, chlorotrimethylsilane or p-toluenesulfonic acid.

In some embodiments, the metathesis reaction is a ring-opening metathetic polymerization of dicyclopentadiene.

In yet some other embodiments, the (pre)catalyst of the general formula (I) or the compounds of the general formula (II) is added in the solid form to dicyclopentadiene.

In one embodiment, the polymerization reaction is initiated by heating the mixture of dicyclopentadiene and the (pre)catalyst of the general formula (I) or the compounds of the general formula (II) to a temperature of 30° C. or higher.

In some embodiments, the starting material contains at least 94 wt. % of dicyclopentadiene.

In another embodiment, the metathesis reaction is carried out at a temperature of from 20 to 120° C. In yet another embodiment, the metathesis reaction is carried out in a period of from 1 minute to 24 hours.

In some embodiments, the metathesis reaction is carried out in the presence of an additive promoting formation of cross bonds.

In one embodiment, the metathesis reaction is carried out using the amount of the (pre)catalyst equal to or less than 1000 ppm.

Throughout the description of the invention and patent claims, if ppm (parts per million) units are used with relation to amount of substance, these are on a weight basis.

Since the inventors do not wish to be bound by any particular mechanism of catalysis, the "(pre)catalyst" term is used to indicate that the compound according to the invention may be either the catalyst itself or a precursor of the active species being the actual catalyst.

The definitions of groups not defined below should have the broadest meanings known in the art.

The term "optionally substituted" means that one or more hydrogen atoms of the group in question have been replaced with the specified groups, provided that such a substitution results in formation of a stable compound.

The term "halo" or "halogen" represents an element selected from F, C$_1$, Br, I.

The term "alkyl" concerns a saturated, straight-chain or branched-chain hydrocarbon substituent having the specified number of carbon atoms. The non-limiting examples of alkyls are: methyl, ethyl, propyl, isopropyl, butyl, sec-butyl, tert-butyl, pentyl.

The term "alkoxy" concerns the alkyl substituent, as defined above, bound via an oxygen atom.

The term "perfluoroalkyl" represents the alkyl, as defined above, wherein all hydrogens have been replaced with halogen atoms, where the halogen atoms may be identical or different.

The term "cycloalkyl" concerns a saturated mono- or polycyclic hydrocarbon substituent having the specified number of carbon atoms. The non-limiting examples of a cycloalkyl substituent are cyclopropyl, cyclobutyl, cyclopentyl, cyclohexyl.

The term "alkenyl" concerns a non-cyclic, straight or branched hydrocarbon chain having the specified number of carbon atoms and containing at least one carbon-carbon double bond. The non-limiting examples of alkenyls are: vinyl, allyl, 1-butenyl, 2-butenyl.

The term "aryl" concerns an aromatic mono- or polycyclic hydrocarbon substituent having the specified number of carbon atoms. The non-limiting examples of aryl are: phenyl, mesityl, anthracenyl.

The term "heterocyclyl" concerns aromatic as well as non-aromatic cyclic substituents having the specified number of carbon atoms, wherein one or more carbon atoms have been replaced with a heteroatom such as nitrogen, phosphorus, sulfur, oxygen, provided that there are no two directly connected oxygen or sulfur atoms in the ring. Non-aromatic heterocyclyls can contain from 4 to 10 atoms in the ring, whereas aromatic heterocyclyls must have at least 5 atoms in the ring. The benzo-fused systems also belong to heterocyclyls. The non-limiting examples of non-aromatic heterocyclyls are: pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, 2-pyrrolinyl, indolinyl. The non-limiting examples of aromatic heterocyclyls are: pyridinyl, imidazolyl, pyrimidinyl, pyrazolyl, triazolyl, pyrazinyl, furyl, thienyl. The above-mentioned groups may be bound via a carbon atom or a nitrogen atom. For example, the substituent obtained by binding pyrrole may be either pyrrol-1-yl (N-bound) or pyrrol-3-yl (C-bound).

The term "neutral ligand" concerns a substituent having no electrical charge, capable of coordinating to a ruthenium atom. The non-limiting examples of such ligands are: N-heterocyclic carbene ligands, amines, imines, phosphines and oxides thereof alkyl and aryl phosphites and phosphates, ethers, alkyl and aryl sulfides, coordinated hydrocarbons, haloalkanes and haloarenes. The term "neutral ligand" encompasses also N-heterocyclic compounds; their non-limiting examples are: pyridine, 4-(N,N-dimethylamino)pyridine (DMAP), 3-bromopyridine, piperidine, morpholine, pyridazine, pyrimidine, pyrazine, piperazine, 1,2,3-triazole, 1,3,4-triazole, 1,2,3-triazine and 1,2,4-triazine.

The term "anionic ligand" concerns the substituent capable to co-ordination with a metal center, bearing an electrical charge capable to compensate the charge of the metal center, wherein such a compensation may be complete or partial. The non-limiting examples of anionic ligands are: fluoride, chloride, bromide or iodide anions, carboxylic acid anions, alcohol and phenol anions, thiol and thiophenol anions, (organo)sulfuric and (organo)phosphoric acid anions as well as anions of esters thereof.

The term "carbene" concerns a molecule containing a neutral carbon atom having the valence number of 2 and two non-paired valence electrons. The term "carbene" encompasses also carbene analogues, wherein the carbon atom is replaced with another chemical element such as: boron, silicon, nitrogen, phosphorus, sulfur. The term "carbene" relates particularly to N-heterocyclic carbene (NHC) ligands. The non-limiting examples of the NHC ligands are:

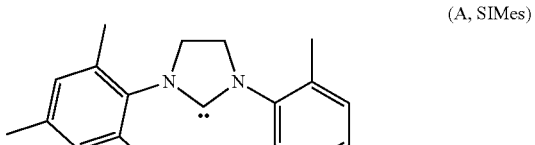

(A, SIMes)

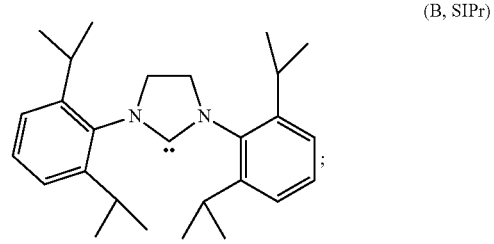

(B, SIPr)

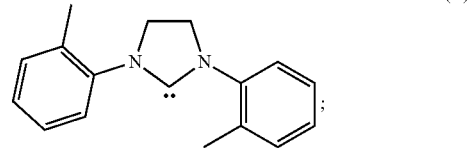

(C)

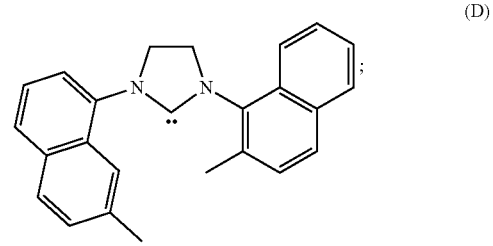

(D)

-continued

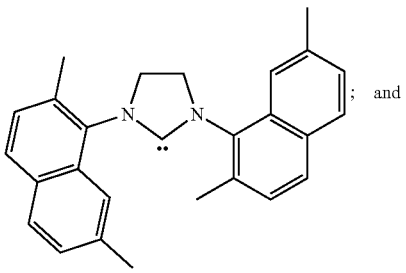

The following examples describe the procedures used for the preparation of the compounds of this invention. The following examples are only intended to illustrate the invention and to explain its particular aspects.

EXAMPLE 1

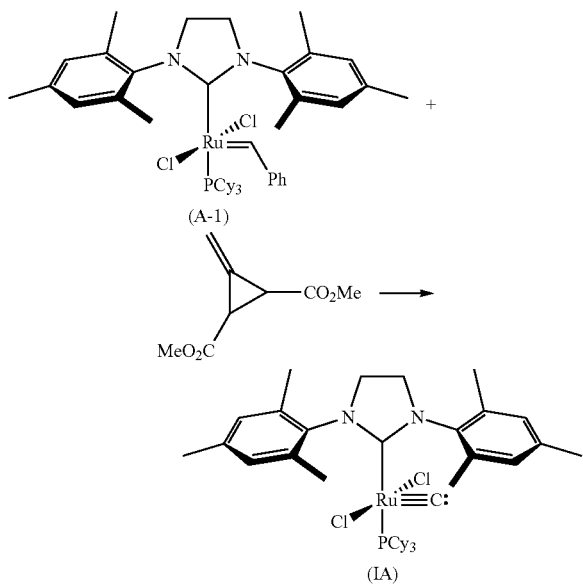

To a solution of dimethyl 3-methylenecyclopropane-1,2-dicarboxylate (0.613 g, 3.6 mmol, 1.8 equiv.) in dry, deoxygenated dichloromethane (20 mL) complex (A-1) (1.698 g, 2 mmol, 1 equiv.) was added as solid. The mixture was refluxed under argon atmosphere for 2 h. After that time the mixture was cooled down to rt. From that point all operations were carried out in air atmosphere. Volume of the dichloromethane was reduced to ca. 5 mL and methanol (5 mL) was added. The remaining dichloromethane was slowly removed using rotary evaporator and crystals formed were filtered, washed with methanol (3×1 mL) and dried in vacuum. The title compound (IA) was obtained as yellow crystalline solid, 1.37 g (89%), and was characterized by NMR as follows:

$^1$H NMR (601 MHz, CDCl$_3$): 6.95 (s, 2H), 6.89 (s, 2H), 4.14-4.00 (m, 4H), 2.54 (s, 6H), 2.49 (s, 6H), 2.34-2.26 (m, 6H), 2.24 (s, 3H), 1.92-1.84 (m, 6H), 1.72-1.64 (m, 6H), 1.64-1.58 (m, 3H), 1.24-1.06 (m, 15H).

$^{13}$C NMR (151 MHz, CDCl$_3$): 479.2, 212.6, 212.0, 138.3, 138.2, 138.0, 137.9, 137.2, 136.8, 135.1, 129.3, 129.2, 128.4, 127.7, 126.1, 113.7, 53.4, 52.0, 51.9, 50.9, 50.8, 31.1, 31.0, 29.3, 27.9, 27.8, 26.3, 21.2, 20.9, 19.7, 18.7.

$^{31}$P NMR (243 MHz, CDCl$_3$): 34.1.

EXAMPLE 2

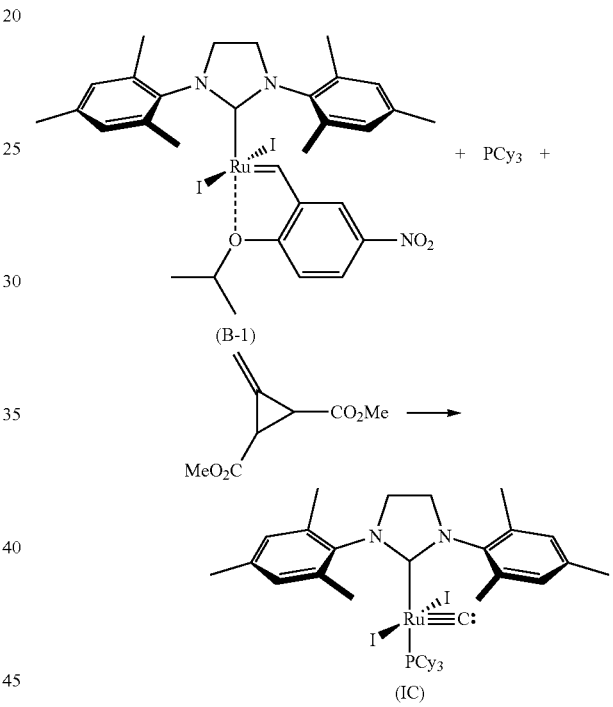

To a solution of complex (B-1) (1.71 g, 2 mmol, 1 equiv.) in dry, deoxygenated dichloromethane (20 mL) tricyclohexylphosphine (0.673 g, 2.4 mmol, 1.2 equiv.) was added as solid under argon atmosphere. The mixture was stirred for 10 min at rt and dimethyl 3-methylenecyclopropane-1,2-dicarboxylate (0.681 g, 4 mmol, 2 equiv.). The mixture was refluxed under argon atmosphere for 3 h. After that time the mixture was cooled down to rt. From that point all operations were carried out in air atmosphere. Volume of the dichloromethane was reduced to ca. 5 mL and methanol (5 mL) was added. The remaining dichloromethane was slowly removed using rotary evaporator and crystals formed were filtered, washed with methanol (3×1 mL) and dried in vacuum. The title compound (IC) was obtained as orange crystalline solid, 1.61 g (84%), and was characterized by NMR as follows:

$^1$H NMR (601 MHz, CDCl$_3$): 6.93 (s, 2H), 6.84 (s, 2H), 4.19-4.11 (m, 2H), 4.09-4.02 (m, 2H), 2.98-2.76 (br, 3H), 2.71 (s, 6H), 2.61 (s, 6H), 2.26 (s, 3H), 2.23 (s, 3H), 1.95 (br, 6H), 1.75-1.60 (m, 9H), 1.26-1.08 (m, 15H).

$^{13}$C NMR (151 MHz, CDCl$_3$): 475.8, 211.4, 210.9, 138.1, 137.9, 137.8, 137.7, 137.1, 135.8, 129.5, 129.4, 53.4, 52.5, 52.4, 51.6, 51.5, 33.9, 33.8, 30.5, 27.8, 27.8, 26.4, 22.7, 21.1, 21.0, 20.8.

$^{31}$P NMR (243 MHz, CDCl$_3$): 32.3.

EXAMPLE 3

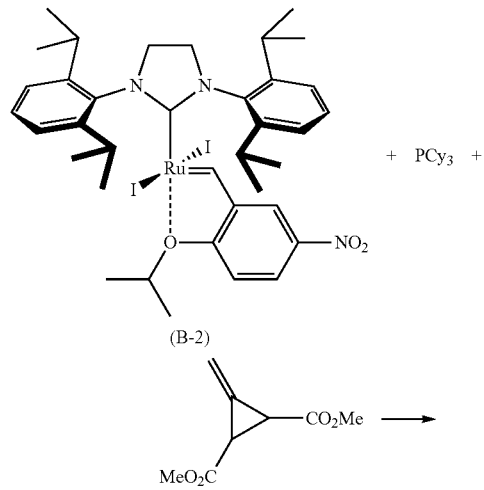

To a solution of complex (B-2) (1.88 g, 2 mmol, 1 equiv.) in dry, deoxygenated dichloromethane (20 mL) tricyclohexylphosphine (0.673 g, 2.4 mmol, 1.2 equiv.) was added as solid under argon atmosphere. The mixture was stirred for 10 min at rt and dimethyl 3-methylenecyclopropane-1,2-dicarboxylate (0.442 g, 2.6 mmol, 1.3 equiv.). The mixture was refluxed under argon atmosphere for 18 h. After that time the mixture was cooled down to rt. From that point all operations were carried out in air atmosphere. Volume of the dichloromethane was reduced to ca. 5 mL and methanol (5 mL) was added. The remaining dichloromethane was slowly removed using rotary evaporator and crystals formed were filtered, washed with methanol (3×1 mL) and dried in vacuum. The title compound (ID) was obtained as orange crystalline solid, 1.74 g (84%), and was characterized by NMR as follows:

$^1$H NMR (601 MHz, CDCl$_3$): 7.38-7.30 (m, 1H), 7.29-7.20 (m, 3H), 7.18-7.10 (m, 2H), 4.30-4.12 (m, 4H), 3.90 (septet, J=6.6 Hz, 4H), 2.75 (q, J=11.9 Hz, 3H), 1.96-1.87 (m, 6H), 1.70-1.62 (m, 6H), 1.61-1.55 (m, 3H), 1.50 (d, J=6.5 Hz, 5H), 1.31 (dd, J=12.1, 6.7 Hz, 11H), 1.26-1.02 (m, 23H).

$^{13}$C NMR (151 MHz, CDCl$_3$): 471.2, 214.6, 214.1, 149.0, 147.7, 139.1, 135.9, 129.4, 129.2, 124.6, 123.6, 55.3 (2C), 53.8 (2C), 53.4, 34.4, 34.3, 30.7, 29.7, 28.2, 27.8, 27.7 (2C), 26.4, 26.2, 25.1, 23.4.

$^{31}$P NMR (243 MHz, CDCl$_3$): 32.8.

EXAMPLE 4

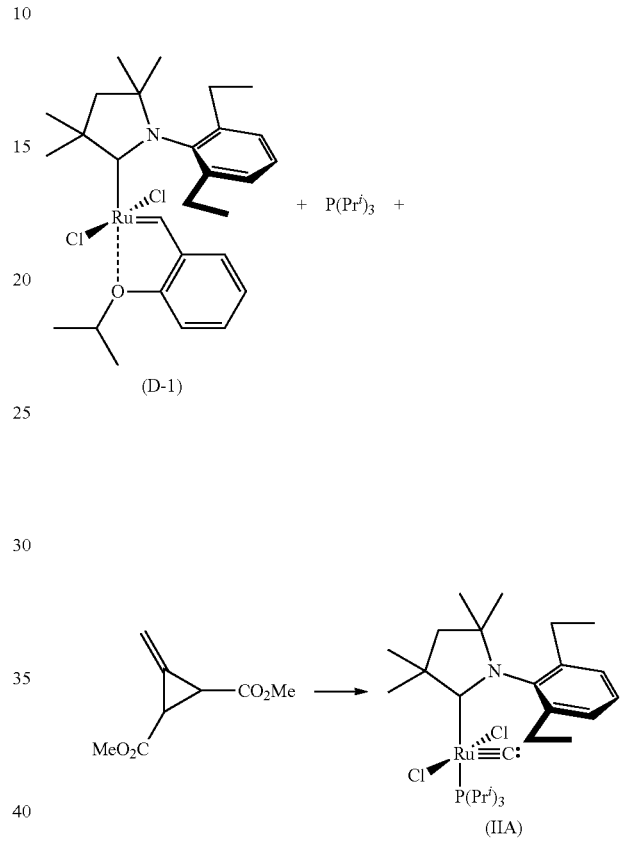

To a solution of complex (D-1) (1.16 g, 2 mmol, 1 equiv.) in dry, deoxygenated dichloromethane (20 mL) triisopropylphosphine (0.497 mL, 0.417 g, 2.6 mmol, 1.3 equiv.) was added followed by dimethyl 3-methylenecyclopropane-1,2-dicarboxylate (0.442 g, 2.6 mmol, 1.3 equiv.). The mixture was stirred at rt under argon atmosphere for 18 h. From that point all operations were carried out in air atmosphere. Volume of the dichloromethane was reduced to ca. 5 mL and methanol (5 mL) was added. The remaining dichloromethane was slowly removed using rotary evaporator and crystals formed were filtered, washed with methanol (3×1 mL) and dried in vacuum. The title compound (IIA) was obtained as yellow crystalline solid, 1.09 g (90%), and was characterized by NMR as follows:

$^1$H NMR (601 MHz, CD$_2$Cl$_2$): 7.38-7.33 (m, 1H), 7.33-7.28 (2H), 2.85 (dq, J=14.7, 7.3 Hz, 2H), 2.73 (ddt, J=14.5, 11.0, 7.3 Hz, 3H), 2.53 (dq, J=14.8, 7.4 Hz, 2H), 2.09 (s, 2H), 1.73 (s, 6H), 1.38-1.30 (m, 24H), 1.17 (t, J=7.4 Hz, 6H).

$^{13}$C NMR (151 MHz, CD$_2$Cl$_2$): 473.5, 265.7, 265.2, 142.7, 139.6, 129.0, 126.6, 80.9 (2C), 58.7, 58.6, 52.50 (2C), 31.2, 29.1, 25.5, 22.5, 22.4, 19.8, 14.9.

$^{31}$P NMR (243 MHz, CD$_2$C$_2$): 40.6.

EXAMPLE 5

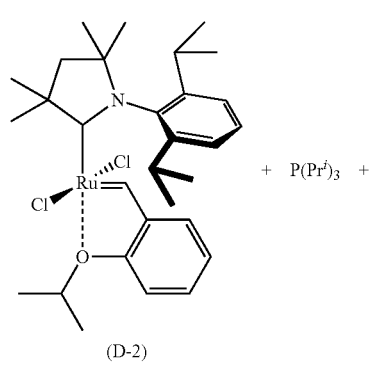

To a solution of complex (D-2) (1.51 g, 2.5 mmol, 1 equiv.) in dry, deoxygenated toluene (25 mL) triisopropylphosphine (0.621 mL, 0.521 g, 3.25 mmol, 1.3 equiv.) was added followed by dimethyl 3-methylenecyclopropane-1,2-dicarboxylate (0.553 g, 3.25 mmol, 1.3 equiv.). The mixture was stirred at 80° C. under argon atmosphere for 18 h. After that time the mixture was cooled down to rt. From that point all operations were carried out in air atmosphere. Toluene was evaporated in vacuum and the residue was re-dissolved in small amount of dichloromethane (ca. 7.mL). Methanol (7.mL) was added and dichloromethane was slowly removed using rotary evaporator. Crystals formed were filtered, washed with methanol (3×1.5 mL) and dried in vacuum. The title compound (IB) was obtained as yellow crystalline solid, 1.32 g (84%), and was characterized by NMR as follows:

$^1$H NMR (601 MHz, $C_6D_6$): 7.20-7.17 (m, 2H), 7.15-7.12 (m, 1H), 3.26 (septet, J=6.4 Hz, 2H), 2.68 (ddt, J=14.5, 10.8, 7.3 Hz, 3H), 1.93 (s, 6H), 1.66 (s, 2H), 1.58 (d, J=6.3 Hz, 6H), 1.30-1.24 (m, 24H), 1.03 (s, 6H).

$^{13}$C NMR (151 MHz, $C_6D_6$): 472.2, 268.3, 267.8, 147.8, 137.1 (2C), 130.00, 125.7, 79.8 (2C), 58.7 (2C), 52.3 (2C), 31.0, 30.2, 29.2, 27.7, 25.0, 22.6, 22.5, 20.0.

$^{31}$P NMR (243 MHz, $C_6D_6$): 39.8.

EXAMPLE 6

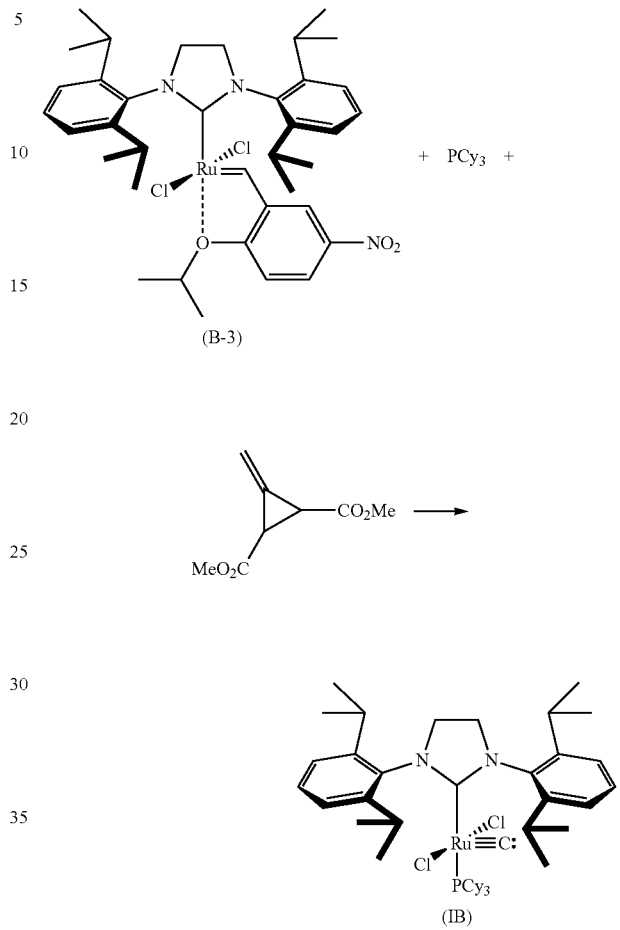

To a solution of complex (B-3) (1.89 g, 2.5 mmol, 1 equiv.) in dry, deoxygenated dichloromethane (25 mL) tricyclohexylphosphine (0.841 g, 3 mmol, 1.2 equiv.) was added as solid under argon atmosphere. The mixture was stirred for 10 min at rt and dimethyl 3-methylenecyclopropane-1,2-dicarboxylate (0.553 g, 3.25 mmol, 1.3 equiv.). The mixture was refluxed under argon atmosphere for 2 h. After that time the mixture was cooled down to rt. From that point all operations were carried out in air atmosphere. Volume of the dichloromethane was reduced to ca. 7 mL and methanol (7 mL) was added. The remaining dichloromethane was slowly removed using rotary evaporator and crystals formed were filtered, washed with methanol (3×1.5 mL) and dried in vacuum. The title compound (B) was obtained as yellow crystalline solid, 1.81 g (85%), and was characterized by NMR as follows:

$^1$H NMR (601 MHz, $CDCl_3$): 7.48-7.06 (m, 6H), 4.34-3.98 (m, 4H), 3.90-3.35 (m, 4H), 2.30-2.19 (m, 3H), 1.89-1.80 (m, 6H), 1.65-1.00 (m, 48H).

$^{13}$C NMR (151 MHz, $CDCl_3$): 476.2, 215.0, 214.4, 149.1, 147.8, 138.8, 135.1, 129.3, 124.2, 123.5, 54.4, 53.7, 31.3, 31.2, 29.4, 29.3, 28.1, 27.7, 27.6, 27.4, 26.3, 25.8, 23.4, 23.1.

$^{31}$P NMR (243 MHz, $CDCl_3$): 35.4.

EXAMPLE 7

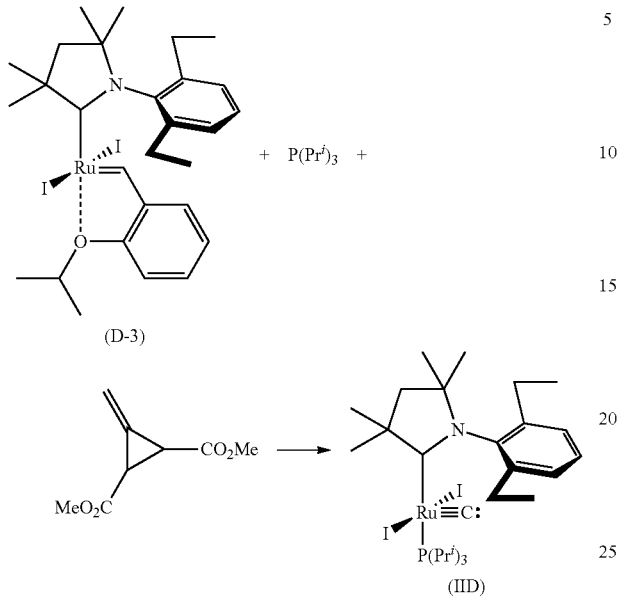

To a solution of complex (D-3) (1.1 g, 1.45 mmol, 1 equiv.) in dry, deoxygenated dichloromethane (15 mL) tri-isopropylphosphine (0.359 mL, 0.301 g, 1.88 mmol, 1.3 equiv.) was added followed by dimethyl 3-methylenecyclopropane-1,2-dicarboxylate (0.32 g, 1.88 mmol, 1.3 equiv.). The mixture was stirred at rt under argon atmosphere for 18 h. From that point all operations were carried out in air atmosphere. Volume of the dichloromethane was reduced to ca. 5 mL and methanol (5 mL) was added. The remaining dichloromethane was slowly removed using rotary evaporator and crystals formed were filtered, washed with methanol (3×1 mL) and dried in vacuum. The title compound (IID) was obtained as orange crystalline solid, 0.945 g (83%), and was characterized by NMR as follows:

$^1$H NMR (601 MHz, CD$_2$Cl$_2$): 7.34-7.26 (m, 3H), 3.30-3.12 (m, 5H), 2.66 (dq, J=14.9, 7.4 Hz, 2H), 2.11 (s, 2H), 1.87 (s, 6H), 1.41 (s, 6H), 1.37-1.31 (m, 18H), 1.22 (t, J=7.4 Hz, 6H).

$^{31}$P NMR (243 MHz, CD$_2$Cl$_2$): 36.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula I:

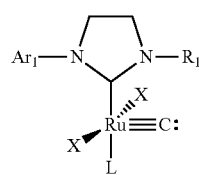

wherein:

X is chlorine, bromine or iodine;

L is PR$_3$, where each R is independently selected from the group consisting of isopropyl, sec-butyl, tert-butyl, cyclohexyl, bicyclo(C$_5$-C$_{10}$)alkyl, phenyl, benzyl, isopropoxy, sec-butoxy, tert-butoxy, cyclohexyloxy, phenoxy and benzyloxy;

R$_1$ is selected from the group consisting of methyl, ethyl, isopropyl, sec-butyl, tert-butyl, substituted or unsubstituted cyclohexyl, substituted or unsubstituted phenyl, substituted or unsubstituted biphenyl and substituted or unsubstituted naphthyl;

Ar$_1$ is selected from the group consisting of substituted or unsubstituted phenyl, substituted or unsubstituted biphenyl and substituted or unsubstituted naphthyl;

wherein said substituents are selected from the group consisting of methyl, ethyl, iso-propyl, tert-butyl and phenyl; and with the proviso that when X is chlorine, R$_1$ is not 2,4,6-trimethylphenyl.

2. The compound according to claim 1, wherein:

X is chlorine or iodine;

R$_1$ and Ar$_1$ are both substituted phenyl; and

L is PR$_3$, where each R is independently selected from the group consisting of isopropyl, sec-butyl, tert-butyl, cyclohexyl and phenyl.

3. The compound according to claim 1, wherein:

X is chlorine;

R$_1$ and Ar$_1$ are independently selected from the group consisting of phenyl, 2-methylphenyl, 2,4-dimethylphenyl, 2,6-dimethylphenyl, 2,4,6-trimethylphenyl, 2-ethylphenyl, 2,4-diethylphenyl, 2,6-diethylphenyl, 2,4,6-triethylphenyl, 2-isopropylphenyl and 2,6-diisopropylphenyl; and L is tri(isopropyl)phosphine or tricyclohexylphosphine.

4. The compound according to claim 1, wherein:

X is chlorine;

R$_1$ and Ar$_1$ are independently selected from the group consisting of phenyl, 2,4-dimethylphenyl, 2,6-dimethylphenyl, 2,4,6-trimethylphenyl, 2,4-diethylphenyl, 2,6-diethylphenyl, 2,4,6-triethylphenyl, 2-isopropylphenyl and 2,6-diisopropylphenyl; and L is tricyclohexylphosphine.

5. The compound according to claim 1, wherein:

X is iodine;

R$_1$ and Ar$_1$ are independently selected from the group consisting of 2,6-dimethylphenyl, 2,4,6-trimethylphenyl, 2,6-diethylphenyl, 2,4,6-triethylphenyl and 2,6-diisopropylphenyl; and L is tricyclohexylphosphine.

6. The compound according to claim 1, which is selected from the group consisting of:

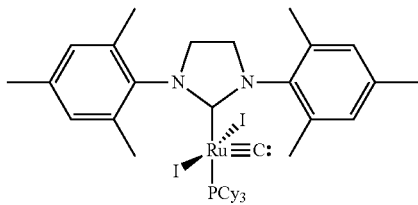

1,3-bis(2,4,6-trimethylphenyl)-imidazolidin-2-ylidene-tricyclohexylphosphine-ruthenium carbide diiodide;

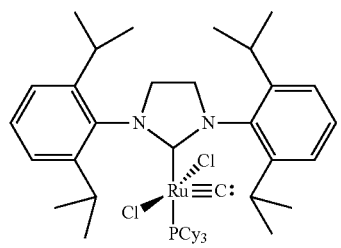

1,3-bis(2,6-diisopropylphenyl)-imidazolidin-2-ylidene-tricyclohexylphosphine-ruthenium carbide dichloride;

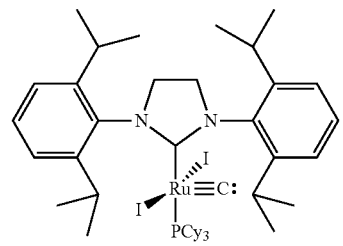

1,3-bis(2,6-diisopropylphenyl)-imidazolidin-2-ylidene-tricyclohexylphosphine-ruthenium carbide diiodide.

7. A process for carrying out a metathesis reaction of olefins, comprising contacting at least one olefin with the compound of claim 1 as a precatalyst.

8. The process according to claim 7, wherein the metathesis reaction is carried out in an organic solvent.

9. The process according to claim 8, wherein the organic solvent is selected from the group consisting of dichloromethane, dichloroethane, toluene, ethyl acetate and a mixture in any combination thereof.

10. The process according to claim 7, wherein the metathesis reaction is carried out in the presence of a chemical activator.

11. The process according to claim 7, wherein the chemical activator is a Bronsted or Lewis acid or a halo-derivative of alkane or silane.

* * * * *